United States Patent
Massarwa et al.

(10) Patent No.: US 9,895,079 B2
(45) Date of Patent: Feb. 20, 2018

(54) ELECTROPOTENTIAL MAPPING

(71) Applicant: BIOSENSE WEBSTER (ISRAEL), LTD., Yokneam (IL)

(72) Inventors: Fady Massarwa, Baka el Gharbiya (IL); Ido Ilan, Yokneam (IL)

(73) Assignee: Biosense Webster (Israel) Ltd. (IL)

( * ) Notice: Subject to any disclaimer, the term of this patent is extended or adjusted under 35 U.S.C. 154(b) by 979 days.

(21) Appl. No.: 13/626,959

(22) Filed: Sep. 26, 2012

(65) Prior Publication Data

US 2014/0088447 A1    Mar. 27, 2014

(51) Int. Cl.
*A61B 5/053* (2006.01)
*A61B 5/04* (2006.01)
*A61B 5/00* (2006.01)
*A61B 5/0402* (2006.01)
*A61B 5/06* (2006.01)

(52) U.S. Cl.
CPC .......... *A61B 5/0538* (2013.01); *A61B 5/0044* (2013.01); *A61B 5/0402* (2013.01); *A61B 5/04012* (2013.01); *A61B 5/04028* (2013.01); *A61B 5/062* (2013.01); *A61B 5/063* (2013.01)

(58) Field of Classification Search
CPC ......... A61B 5/063; A61B 5/061; A61B 5/065; A61B 19/5244; A61B 5/0538; A61B 5/0402; A61B 5/0044; A61B 5/04012; A61B 5/062; A61B 5/04028
USPC ....................................................... 600/508
See application file for complete search history.

(56) References Cited

U.S. PATENT DOCUMENTS

| | | | | |
|---|---|---|---|---|
| 4,697,597 A * | 10/1987 | Sanz et al. | ..................... | 600/512 |
| 4,961,428 A * | 10/1990 | Nikias et al. | ................. | 600/512 |
| 5,711,304 A | 1/1998 | Dower | | |
| 5,803,084 A * | 9/1998 | Olson | ........................... | 600/512 |
| 6,226,542 B1 * | 5/2001 | Reisfeld | ........................ | 600/407 |
| 6,240,307 B1 | 5/2001 | Beatty et al. | | |
| 7,841,986 B2 * | 11/2010 | He et al. | ........................ | 600/508 |
| 8,401,625 B2 * | 3/2013 | Harlev et al. | ................. | 600/509 |
| 8,577,450 B1 * | 11/2013 | Chmiel et al. | ................ | 600/523 |
| 2002/0055674 A1 * | 5/2002 | Ben-Haim et al. | .......... | 600/374 |
| 2003/0078494 A1 * | 4/2003 | Panescu et al. | ............. | 600/424 |
| 2006/0058692 A1 * | 3/2006 | Beatty et al. | ................. | 600/508 |
| 2007/0106289 A1 * | 5/2007 | O'Sullivan | ..................... | 606/41 |
| 2007/0197929 A1 * | 8/2007 | Porath et al. | ................. | 600/523 |
| 2007/0299351 A1 * | 12/2007 | Harlev et al. | ................. | 600/509 |

(Continued)

FOREIGN PATENT DOCUMENTS

WO    WO 02/041772 A1    5/2002
WO    WO 10/051183 A1    5/2010

OTHER PUBLICATIONS

EP Search Report EP 13 18 6001 dated Jan. 23, 2014.

(Continued)

*Primary Examiner* — Mark W Bockelman
(74) *Attorney, Agent, or Firm* — Louis J. Capezzuto

(57) ABSTRACT

A method for forming an electropotential map, including: measuring locations of points on a surface of a body organ, and measuring electrical potentials of a subset of the points. The method further includes assigning respective resistances to line segments joining the points so as to define a resistor mesh, and generating an electropotential map of the surface by applying an harmonic function to the resistor mesh responsive to the measured electrical potentials.

24 Claims, 5 Drawing Sheets

(56) References Cited

U.S. PATENT DOCUMENTS

| | | | |
|---|---|---|---|
| 2009/0048528 A1* | 2/2009 | Hopenfeld et al. | 600/516 |
| 2010/0168558 A1* | 7/2010 | Olson | 600/424 |
| 2010/0268059 A1* | 10/2010 | Ryu et al. | 600/407 |
| 2010/0312086 A9* | 12/2010 | Beatty et al. | 600/374 |
| 2014/0235989 A1* | 8/2014 | Wodlinger et al. | 600/374 |

OTHER PUBLICATIONS

Oostendorp T.F. et al. Interpolation on a Triangulated 3D Surface. Journal of Computational Physics 80, 331-343 (1989).
Yilmaz, B. et al. Usage of Spline Interpolation in Catheter-Based Cardiac Mapping. Turk J Elec Eng & Comp Sci, vol. 18, No. 6, 2010, pp. 989-1002.

* cited by examiner

ELECTROPOTENTIAL MAPPING

FIELD OF THE INVENTION

The present invention relates generally to graphic displays, and specifically to displaying of electrophysiological data in a map.

BACKGROUND OF THE INVENTION

During a medical procedure on an organ such as the heart, it may be important to map the electrical activity of the organ. A system to improve the accuracy of the mapping would be advantageous.

SUMMARY OF THE INVENTION

An embodiment of the present invention provides a method for forming an electropotential map, including:

measuring locations of points on a surface of a body organ;

measuring electrical potentials of a subset of the points;

assigning respective resistances to line segments joining the points so as to define a resistor mesh; and generating an electropotential map of the surface by applying an harmonic function to the resistor mesh responsive to the measured electrical potentials.

Typically, the body organ consists of a heart of a human subject, and the electropotential map includes a map of respective potentials associated with local activation times of the heart.

In a disclosed embodiment, measuring the locations includes inserting a probe into the body organ, and tracking a distal end of the probe in contact with the surface. The distal end may include tracking coils located therein, and tracking the distal end may consist of receiving and analyzing signals from the tracking coils. Alternatively or additionally, the distal end has an electrode attached thereto, and measuring the electrical potentials consists of measuring the electrical potentials using the electrode. Tracking the distal end may include measuring an impedance between the electrode and electrodes attached to skin of a human subject having the body organ.

In a further disclosed embodiment, the method includes forming the line segments as a triangular mesh.

In a yet further disclosed embodiment, assigning the respective resistances includes assigning the respective resistances to be directly proportional to the respective lengths.

In an alternative embodiment, applying the harmonic function may include applying a Kirchhoff's circuit law to the resistor mesh. Typically, the Kirchhoff's circuit law consists of Kirchhoff's current law. Generating the electropotential map may include using the Kirchhoff's circuit law to determine electrical potentials of the points on the surface not in the subset.

There is further provided, according to an embodiment of the present invention, apparatus for forming an electropotential map, including:

a probe configured:

to measure locations of points on a surface of a body organ, and to measure electrical potentials of a subset of the points; and a processor, configured:

to assign respective resistances to line segments joining the points so as to define a resistor mesh, and to generate an electropotential map of the surface by applying an harmonic function to the resistor mesh responsive to the measured electrical potentials.

The present disclosure will be more fully understood from the following detailed description of the embodiments thereof, taken together with the drawings, in which:

DETAILED DESCRIPTION OF EMBODIMENTS

Overview

An embodiment of the present invention forms an electropotential map of the surface of a body organ, typically the heart of a human subject. To form the map, coordinates of points on the surface of the organ are determined in a procedure, typically by using a distal end of a catheter probe to contact the surface at the points. In addition, and typically during the procedure, an electrode in the distal end measures electrical potentials of a subset of the points.

A processor forms the points into a mesh, typically a triangular mesh, of line segments joining the points. The processor may sub-divide the mesh into smaller components. For example, if the mesh is a triangular mesh the triangles may be divided into smaller triangles, with correspondingly smaller line segments forming the smaller triangles. The processor assigns each of the line segments a respective resistance which is typically directly positively proportional to the length of the line segment, so as to form a resistor mesh. The resistor mesh is in a one-to-one correspondence with the mesh, or the sub-divided mesh, produced by the processor.

The processor applies an harmonic function to the resistor mesh. Usually, applying the harmonic function comprises applying at least one of Kirchhoff's circuit laws, typically the current law, to the resistor mesh. The application enables the processor to evaluate potentials of resistor vertices that correspond to points whose coordinates have been measured, but which are not part of the subset comprising points with measured potentials. The processor uses the evaluated potentials, together with the measured potentials, to generate an electropotential map of the surface of the organ. The processor typically interpolates between the potentials to form a final map.

The inventor believes that forming an electropotential map by applying an harmonic function, such as by applying Kirchhoff's circuit laws, as described herein, gives a map that is more accurate than electropotential maps formed by prior art mapping systems.

System Description

Figure 1:
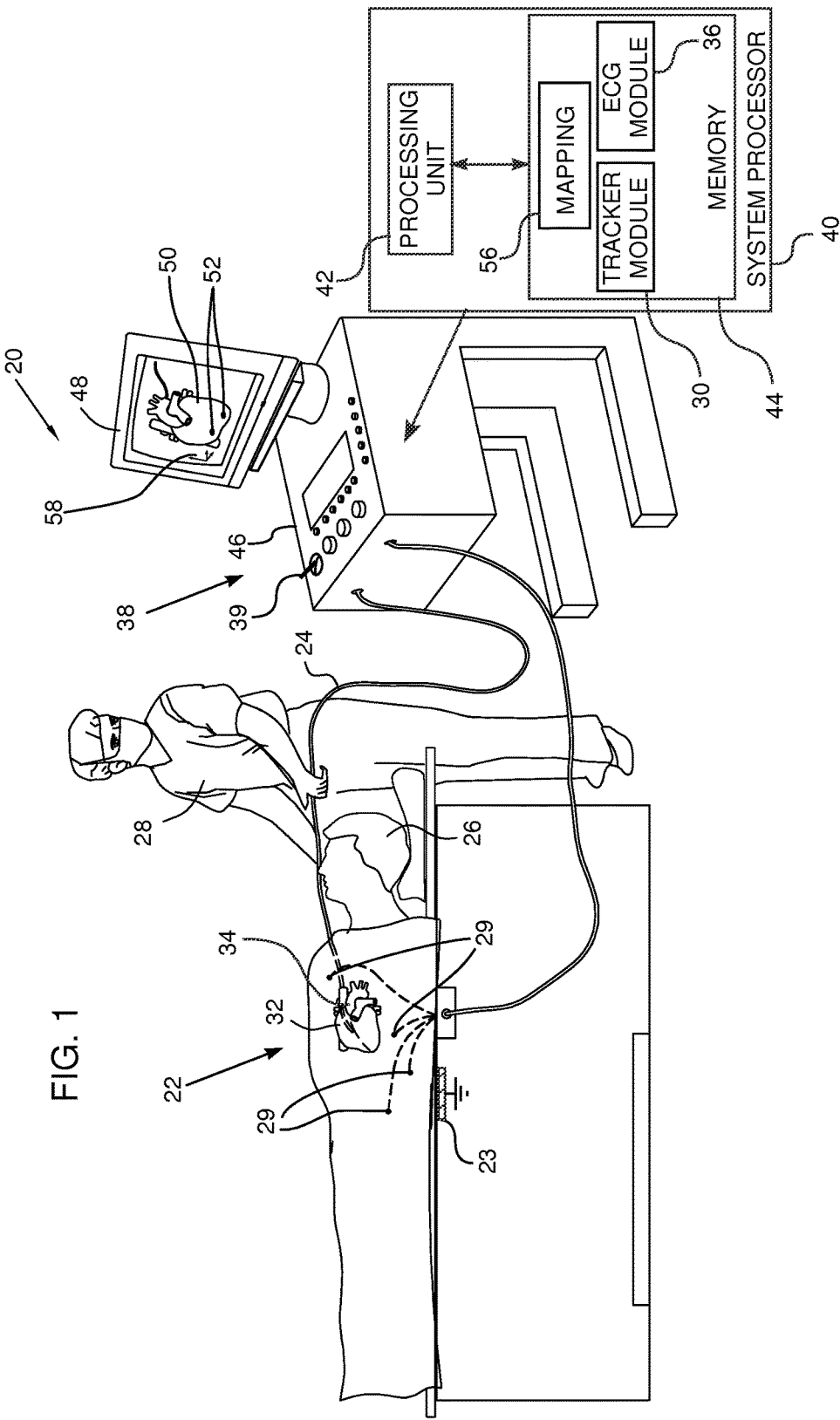
FIG. 1 is a schematic illustration of an electrophysiological mapping system, according to an embodiment of the present invention.

Reference is now made to FIG. 1, which is a schematic illustration of an electrophysiological mapping system 20, according to an embodiment of the present invention. In the description herein, examples of parameters mapped by system 20 are assumed to comprise electropotentials associated with local activation times (LATS) derived from intracardiac electrocardiogram (ECG) potential-time relationships. The measurement and use of LATS and their associated potentials are well known in the electrophysiological arts, and the potential associated with an LAT is herein assigned the symbol $V_{LAT}$. However, system 20 may be configured to map substantially any electropotential parameter or combinations of such parameters for any human or animal organ, and the system is not limited to mapping $V_{LAT}$s.

For simplicity and clarity, the following description, except where otherwise stated, assumes an investigative procedure wherein system 20 senses electrical signals from a body organ 34, herein assumed to comprise a heart, using a probe 24. A distal end 32 of the probe is assumed to have an electrode 22 attached to the distal end for sensing the signals. Those having ordinary skill in the art will be able to adapt the description for multiple probes that may have one or more electrodes, or for a single probe with multiple electrodes, as well as for signals produced by organs other than a heart.

Typically, probe 24 comprises a catheter which is inserted into the body of a human subject 26 during a mapping procedure performed by a user 28 of system 20. In the description herein user 28 is assumed, by way of example, to be a medical professional. During the procedure subject 26 is assumed to be attached to a grounding electrode 23. In addition, electrodes 29 are assumed to be attached to the skin of subject 26, in the region of heart 34.

System 20 may be controlled by a system processor 40, comprising a processing unit 42 communicating with a memory 44. Processor 40 is typically mounted in a console 46, which comprises operating controls 38, typically including a pointing device 39 such as a mouse or trackball, that professional 28 uses to interact with the processor. Results of the operations performed by processor 40 are provided to the professional on a screen which displays a three-dimensional (3D) electrophysiological map 50. Map 50 is herein also termed resultant map 50, to distinguish it from intermediate maps or meshes, described in more detail below, that processor 40 may use in generating map 50. Resultant map illustrates values of the electrophysiological parameters, i.e., $V_{LAT}$s in the example described herein, of heart 34 drawn with respect to a frame of reference 58. The screen typically displays other items 52 of auxiliary information related to the heart and superimposed on the map, while the heart is being investigated, such as the positions of catheters used by professional 28.

Professional 28 is able to use pointing device 39 to vary parameters of the frame of reference, so as to display the resultant map in a selected orientation and/or at a selected magnification.

Screen 48 typically also presents a graphic user interface to the user, and/or a visual representation of the ECG signals sensed by electrode 22.

Processor 40 uses software, including a probe tracker module 30 and an ECG module 36, stored in memory 44, to operate system 20. The software may be downloaded to processor 40 in electronic form, over a network, for example, or it may, alternatively or additionally, be provided and/or stored on non-transitory tangible media, such as magnetic, optical, or electronic memory.

ECG module 36 is coupled to receive electrical signals from electrode 22 and electrodes 29. The module is configured to analyze the signals and may present the results of the analysis in a standard ECG format, typically a graphical representation moving with time, on screen 48.

Probe tracker module 30 tracks sections of probe 24 while the probe is within subject 26. The tracker module typically tracks both the location and orientation of distal end 32 of probe 24, within the heart of subject 26. In some embodiments module 30 tracks other sections of the probe. The tracker module may use any method for tracking probes known in the art. For example, module 30 may operate magnetic field transmitters in the vicinity of the subject, so that magnetic fields from the transmitters interact with tracking coils located in sections of the probe, such as distal end 32, being tracked. The coils interacting with the magnetic fields generate signals which are transmitted to the module, and the module analyzes the signals to determine a location and orientation of the coils. (For simplicity such coils and transmitters are not shown in FIG. 1.) The Carto® system produced by Biosense Webster, of Diamond Bar, Calif., uses such a tracking method. Alternatively or additionally, tracker module 30 may track probe 24 by measuring impedances between electrode 23, electrodes 29 and electrodes 22, as well as the impedances to other electrodes which may be located on the probe. (In this case electrodes 22 and/or electrodes 29 may provide both ECG and tracking signals.) The Carto3® system produced by Biosense Webster uses both magnetic field transmitters and impedance measurements for tracking.

Using tracker module 30 processor 40 is able to measure locations of distal end 32, and form location coordinates of the locations in frame of reference 58 for construction of map 50. The location coordinates are assumed to be stored in a mapping module 56. In addition, mapping module 56 is assumed to store location coordinates of items 52 of auxiliary information associated with heart 34 and with the procedure being performed on the heart.

Other modules in processor 40 measure auxiliary information associated with specific items 52. For clarity and simplicity, other modules measuring the auxiliary information, such as force, temperature, irrigation rate and energy flux modules, are not shown in FIG. 1.

Figure 2:
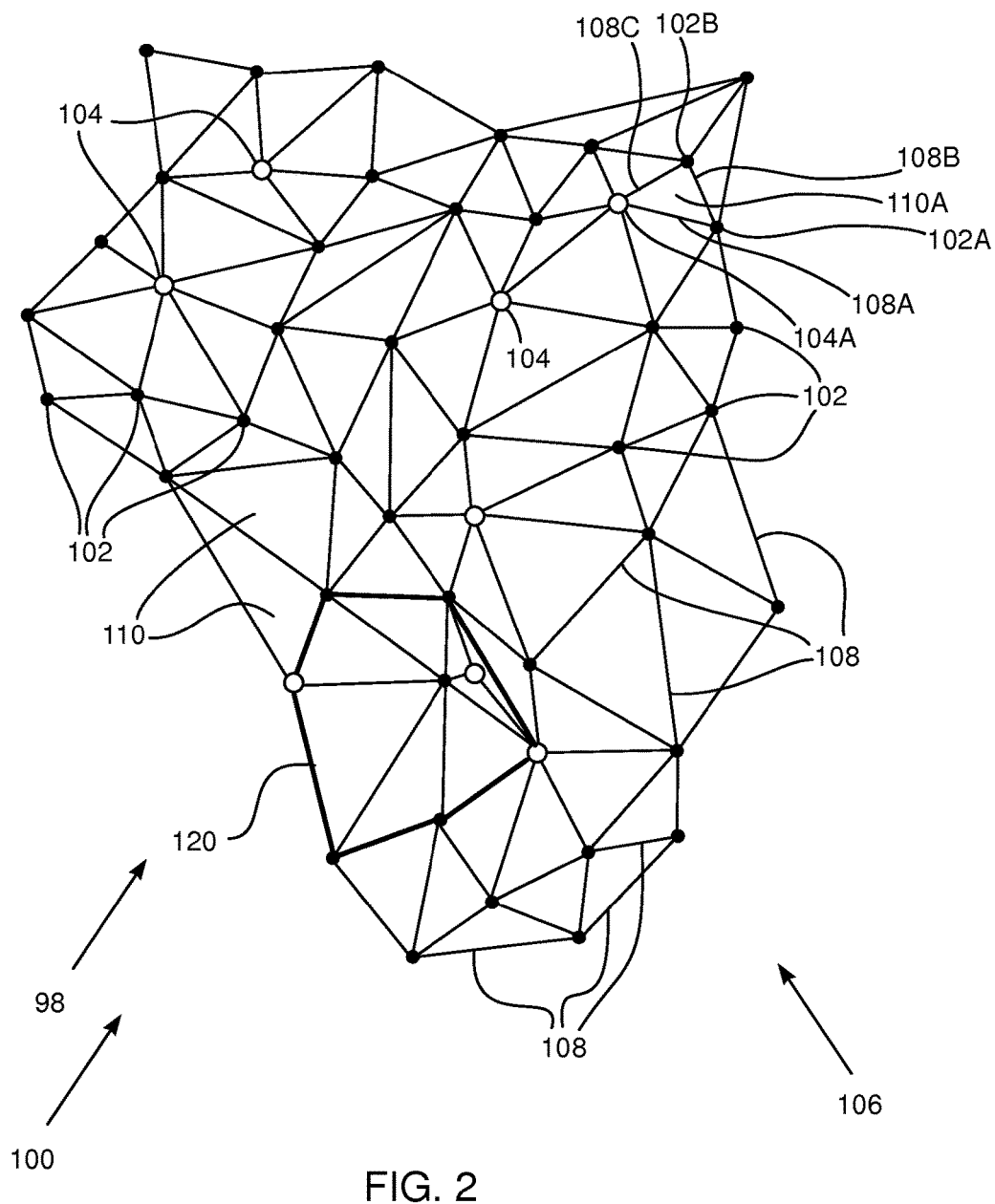
FIG. 2 is a schematic illustration of a section of an initial intermediate map derived from measurements of locations and potentials within a heart, according to an embodiment of the present invention.

FIG. 2 is a schematic illustration of a section 98 of an initial intermediate map 100 derived from measurements of locations and potentials within heart 34, according to an embodiment of the present invention. Typically, to prepare intermediate map 100, user 28 moves the distal end of catheter 24 to touch different heart wall points 102 within heart 34. Points 102 are also herein termed position points 102. Processor 40 uses tracker module 30 to evaluate the location coordinates of the position points. Since the location coordinates typically vary due to the heart beating, the processor also uses ECG module 36 to gate the location coordinates, i.e., to identify the location of a given position point 102 on the heart wall at a predetermined point in time of the heart beat.

In addition to position points 102 of the intermediate map, user 28 also uses the catheter distal tip to measure both the location coordinates and potentials, i.e., in the example described herein $V_{LAT}$s, of other points 104, herein termed potential points 104, on the heart wall. The location coordinates and the potentials are both gated, as described above.

Once processor 40 has registered and stored the location coordinates of the position points and of the potential points, it constructs a coarse mesh 106 comprising line segments 108, also herein termed edges 108, joining the points. The processor may use any convenient method that is known in the art for forming the mesh. By way of example, the method used in an embodiment described herein is assumed to generate a Delaunay triangulation, comprising a plurality of triangles 110 having vertices corresponding to position points 102 and potential points 104. The triangles of the triangulation may be based on Voronoi diagrams formed about points 102 and 104. A method for generating a Delaunay triangulation is described below.

As necessary, in the description herein similar elements are differentiated from each other by appending a letter to the identifying numeral of the element. For example, a triangle 110A has vertices comprising a potential point 104A and position points 102A, 102B, and the triangle is formed of edges 108A, 108B, and 108C.

Mesh 106 comprises a mesh sub-section 120, the perimeter of which is drawn with heavier lines in FIG. 2. Mesh sub-section 120 in described in more detail below.

Figure 3:
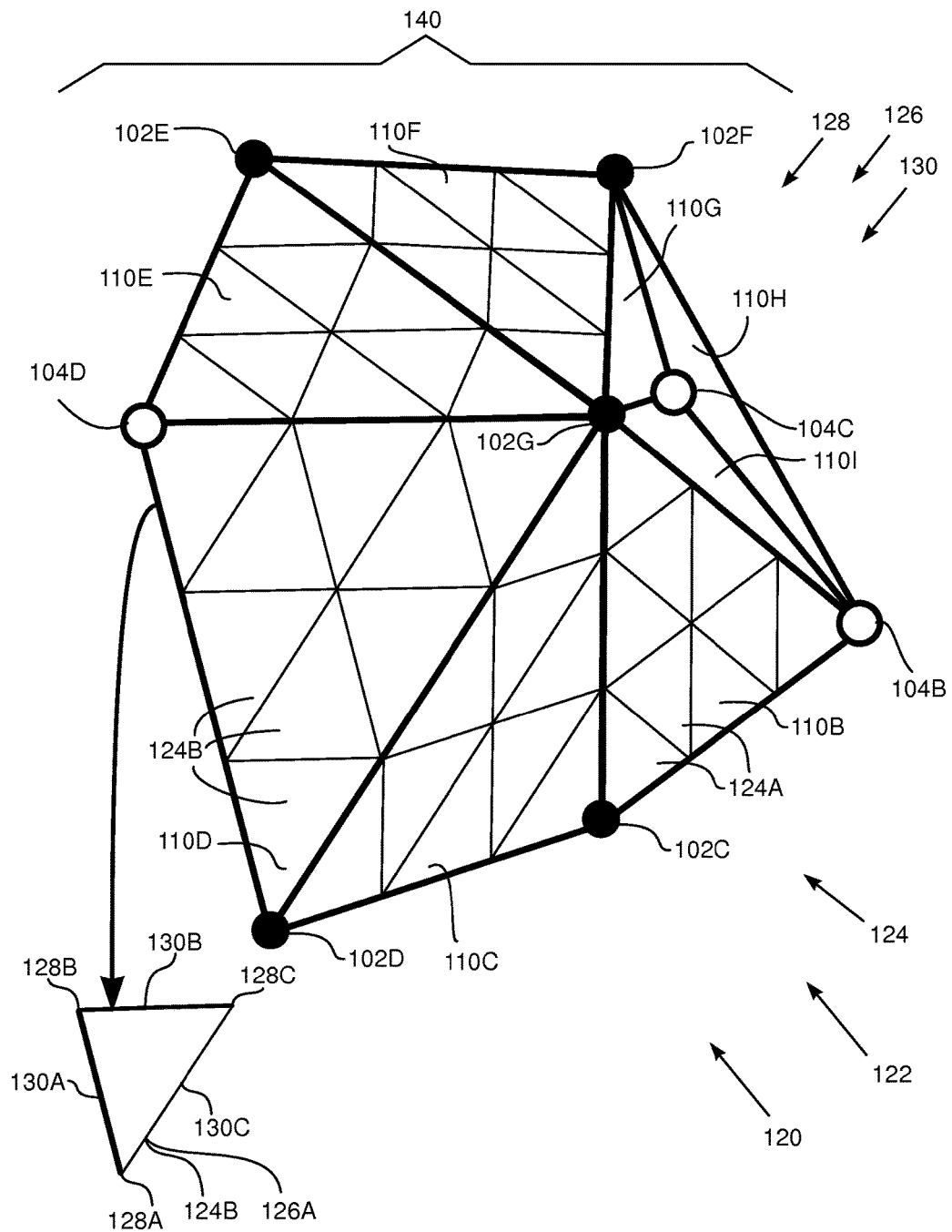
FIG. 3 is a schematic enlarged illustration of a mesh sub-section, according to an embodiment of the present invention.

FIG. 3 is a schematic enlarged illustration of mesh sub-section 120, according to an embodiment of the present invention. Sub-section 120 is a polygon having as vertices potential point 104D, position point 102E, position point 102F, potential point 104B, position point 102C, and position point 102D.

Typically, once processor 40 has generated coarse mesh 106 based on the potential and position points, it sub-divides the mesh to produce an intermediate mesh 122, which is finer than coarse mesh 106. The following description of a sub-division assumes, by way of illustration, that a sub-division is applied to triangles 110B, 110C, 110D, 110E, and 110F of sub-section 120, whereas triangles 110G, 110H, 110I are not sub-divided. In the sub-division each edge of a triangle that is sub-divided is cut, by way of example, into three equal segments, and corresponding end-points of the segments are connected by line segments paralleling the edges of the triangles. As shown in the diagram, this type of sub-division produces, for a given triangle being sub-divided, 9 congruent triangles 124 each of which is similar to the given triangle. Thus triangle 110B forms 9 triangles 124A congruent to each other, and triangle 110D forms 9 triangles 124B congruent to each other. (It will be understood that unless triangles 110B and 110C are congruent, triangles 124A and 124B are not congruent.)

The sub-division described above is one example of a sub-division of coarse mesh 106 that processor 40 may apply, and it will be understood that the processor may implement any convenient sub-division. For example, rather than cutting the edges of triangles in the coarse mesh into three equal segments, the edges may be cut into any other positive integral number (equal to or greater than two) of segments. In some embodiments the original triangles may not be preserved in a sub-division.

Processor 40 may apply the sub-division exemplified above, or another type of sub-division, to some or all of triangles 110 in mesh 106. The application of the sub-division generates sets of triangles 124. Triangles 110 which are not sub-divided remain as undivided triangles 110. The application thus generates sets of triangles which do not enclose other triangles. Such triangles, i.e., triangles which do not enclose other triangles, are topologically equivalent to circles and are herein referred to as simple triangles 126. Any given simple triangle has 3 vertices 128 which are connected by 3 straight line segments 130. In FIG. 3 simple triangles 126 comprise triangles 124, as well as triangles 110G, 110H, and 110I. An exemplary simple triangle 126A, having vertices 128A, 128B (corresponding to potential point 104D), and 128C, connected by straight line segments 130A, 130B, and 130C, is shown in FIG. 3 as a call-out of a specific triangle 124B.

Intermediate mesh 122 thus comprises a set of simple triangles 126 which have at least one common vertex 128. Typically, a given simple triangle 126 has at least one line segment 130 that is common to another simple triangle 126.

The section of intermediate mesh 122 produced by the sub-division of sub-section 120, as described above and as illustrated in FIG. 3, is referred to below as portion 140 of the intermediate mesh.

Figure 4:
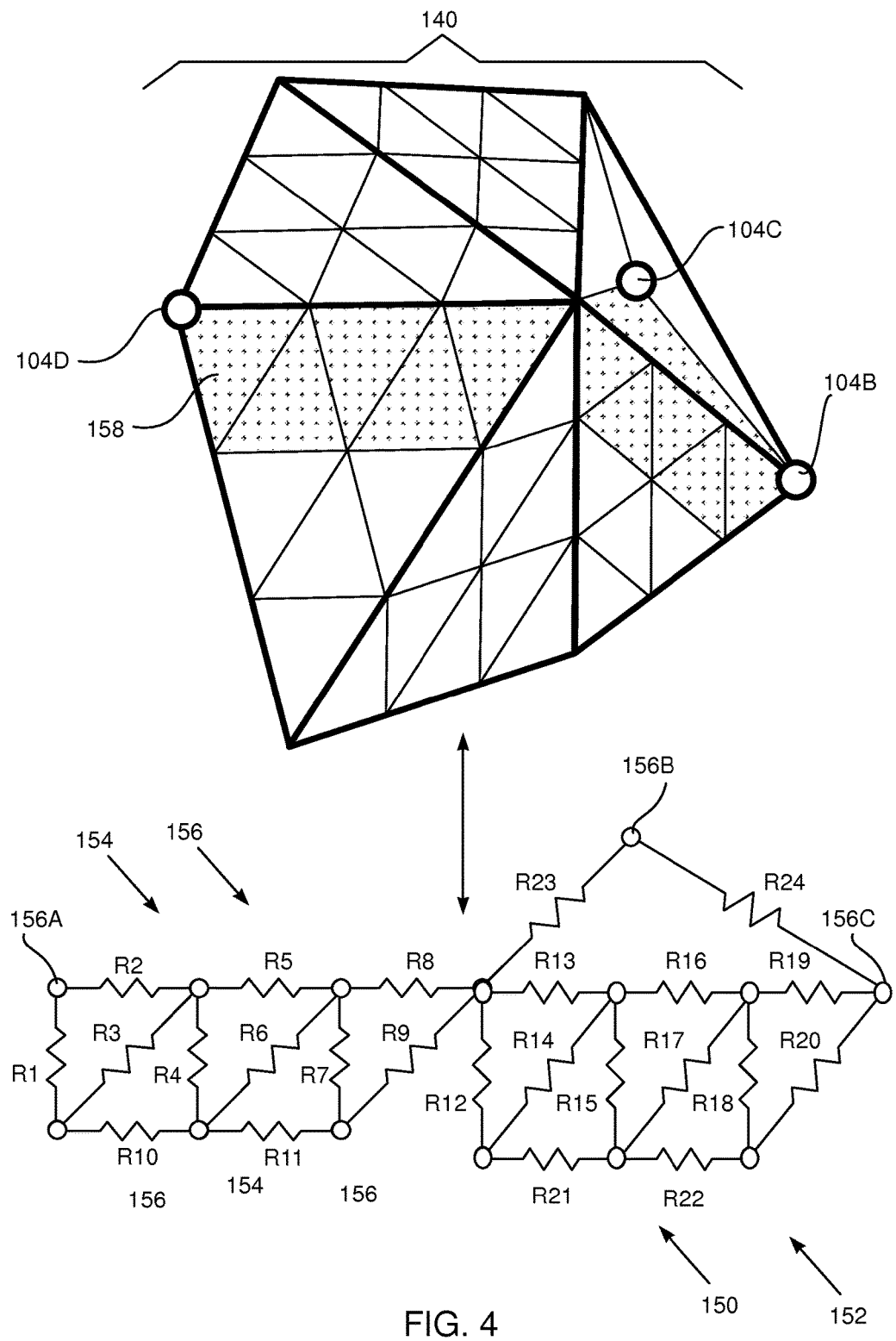
FIG. 4 is a schematic diagram of a portion of a resistor mesh, according to an embodiment of the present invention.

FIG. 4 is a schematic diagram of a portion 152 of a resistor mesh 150, according to an embodiment of the present invention. Processor 40 converts intermediate mesh 122, or mesh 106 if the processor has not generated the intermediate mesh, into resistor mesh 150 comprising resistors 154. Resistors 154 are also identified herein using the letter R with a numeric suffix. In the description herein, any given resistor 154 is assumed to have two end-points 156. For clarity, the following description assumes that the processor generates intermediate mesh 122 by sub-dividing coarse mesh 106 as described above with reference to FIG. 3, and those having ordinary skill in the art will be able to adapt the description, mutatis mutandis, for the case where the coarse mesh is sub-divided by a different method, or where the coarse mesh is not sub-divided.

The intermediate mesh to resistor mesh conversion uses a one-to-one correspondence, so that each vertex 128 corresponds to an end-point 156 of a resistor 154, and each resistor 154 corresponds to a line segment 130. For clarity, in FIG. 4 only portion 152 of resistor mesh 150 is illustrated, portion 152 corresponding to a shaded section 158 of intermediate mesh portion 140.

Shaded section 158 comprises 14 vertices joined by line segments, so that corresponding portion 152 of the resistor mesh comprises 24 resistors, R1, R2, . . . R24, joined at 14 resistor end-points.

Equation (1A) gives the resistance R of a resistor:

$$R = \frac{\rho L}{A} \tag{1A}$$

where $\rho$ is the resistivity of the material of the resistor,
L is a length of the resistor, and
A is the cross-sectional area of the resistor.
Equation (1A) may be rewritten:

$$R = k \cdot L \tag{1B}$$

where k is a parameter.

In an embodiment of the present invention processor may use equation (1A) to assign a respective resistance value to a given resistor of resistor mesh 150 according to the length of the corresponding line segment of the resistor. Typically, all line segments are assumed to have the same constant cross-sectional area. Typically, all line segments are also assumed to have the same resistivity. In some embodiments the resistivity may be varied according to a location of the line segment in the body organ. For simplicity, in the following description wherein equation (1A) is assumed to be used, the resistivity assigned to all resistors is assumed to be equal to 5.6 Ωm, corresponding to an approximate resistivity of heart muscle.

In an alternative embodiment of the present invention, the processor may use equation (1B) to assign a respective resistance value to a given resistor of resistor mesh 150 according to the length of the corresponding line segment of the resistor. If equation (1B) is used, the value of k may be assigned by user 28.

From the dependency on line segment length, certain resistances in resistor mesh 150 are equal in value. For example, in portion 152 equations (2) are true:

$$R2=R5=R8=R10=R11; R1=R4=R7; \text{ and}$$
$$R3=R6=R9. \quad (2)$$

Processor 40 constructs complete resistor mesh 150 by applying equation (1A) or equation (1B), as described above, and equations such as equations (2), to intermediate mesh 122.

Within resistor mesh 150 a subset of resistor end-points 156 correspond to potential points 104. For these resistor end-points the processor assigns the LAT potentials that have been determined for the potential points. Thus, in portion 152, the values $V_{LAT}$(104D), $V_{LAT}$ (104C), and $V_{LAT}$(104B) are respectively assigned to end-points 156A, 156B, and 156C.

Processor 40 then analyzes resistor mesh 150, with its known, assigned, potentials, to evaluate potentials of resistor end-points 156 that are unknown. The unknown resistor end-points correspond to location points 102, as well as to vertices 128 that have been generated by the sub-division of coarse mesh 106. The processor applies the evaluated potentials to vertices of intermediate mesh 122. In other words, the processor analyzes the resistor mesh to find electropotentials of points in the intermediate mesh other than potential points 104 (where the potential is already known).

To analyze the resistor mesh, processor 40 applies an harmonic function to the mesh. Herein, the application of the harmonic function is assumed to correspond to the application of at least one of Kirchhoff's circuit laws, by assuming that the vertices of the mesh can be divided into two types: internal vertices having no external current into the vertices, and boundary vertices, which may have external current.

For any internal vertex i the algebraic sum of the currents into the vertex is zero, so that Kirchhoff's current law may be written:

$$\sum_{j \in Neigh(i)} I_{ij} = 0 \quad (3)$$

where Neigh(i) are the set of vertices neighboring vertex i, i.e., vertices that are directly connected by resistors to vertex i, and where j is an index for the neighboring vertices; Iij is the current between vertex i and vertex j.

Equation (3) may be rewritten:

$$\sum_{j \in Neigh(i)} \frac{v_i - v_j}{R_{ij}} = 0, \text{ i.e.,} \quad (4)$$

$$\sum_{j \in Neigh(i)} \frac{1}{R_{ij}}(v_i - v_j) = 0$$

where $v_i$ is the potential at vertex i,
$v_j$ is the potential at vertex j, and
$R_{ij}$ is the resistance of the resistor between vertex i and vertex j.

Equations (3) and (4) apply for internal vertices. For boundary vertices, where $v_i$ is known, an equation similar to equation (4), but allowing for possible external current into the boundary vertices, is:

$$\sum_{j \in Neigh(i)} \frac{1}{R_{ij}}(v_i - v_j) = I_i \quad (5)$$

where the variables are as defined for equation (4), and where $I_i$ is the current into vertex i.

For a resistor mesh having N vertices equations (4) and (5) combine to define a set of N linear equations, which can be rewritten in matrix form, as:

$$K \cdot v = I \quad (6)$$

where K is a square N×N matrix (also known as the Kirchhoff matrix),
v is a vector of voltages at vertices 1, 2, . . . N, and
I is a vector of currents into the vertices.

Elements of matrix K are defined as follows:

$$k_{i,j} = \begin{cases} \sum_{v_k \in Neigh(v_i)} \frac{1}{R_{ik}}, & i = j \\ -\frac{1}{R_{ij}}, & i \neq j, v_j \in Neigh(v_i) \\ 0, & i \neq j, v_j \notin Neigh(v_i) \end{cases} \quad (7)$$

Voltage vector v comprises values of potentials at boundary vertices, i.e., the measured $V_{LAT}$s of potential points 104, which may be written as a vector $v_b$. Vector $v_b$ is assumed to have $N_b$ values, i.e., $N_b$ is the number measured potential points 104.

Vector v also comprises values of potentials at internal vertices, i.e., the values of $V_{LAT}$ at position points 102, which may be written as a vector $v_i$. Vector $v_i$ is assumed to have $N_i$ values. $N_i$ is the number of internal vertices of the mesh, comprising vertices 128 that are not potential points (vertices 128 include position points 102).

Thus voltage vector v may be rewritten:

$$v \equiv \begin{bmatrix} v_b \\ v_i \end{bmatrix} \quad (8)$$

Current vector I may similarly be rewritten:

$$I \equiv \begin{bmatrix} I_b \\ 0 \end{bmatrix} \quad (9)$$

where the currents into the boundary vertices are a vector $I_b$, with $N_b$ values. By definition, the currents into the internal vertices are zero, and a vector 0 has $N_i$ values, all being equal to 0.

Using equations (8) and (9), equation (6) may be rewritten:

$$K \cdot \begin{bmatrix} v_b \\ v_i \end{bmatrix} = \begin{bmatrix} I_b \\ 0 \end{bmatrix} \quad (10)$$

Matrix K may be rewritten as a matrix of sub-matrices:

$$K \equiv \begin{bmatrix} A & B \\ C & D \end{bmatrix} \quad (11)$$

where A is an $N_b \times N_b$ square sub-matrix, D is an $N_i \times N_i$ square sub-matrix, B is an $N_b \times N_i$ sub-matrix, and C is an $N_i \times N_b$ sub-matrix. The first $N_b$ vertices, i.e., the first rows and first columns of the matrix, correspond to the boundary vertices; the second $N_i$ vertices correspond to the internal vertices.

Substituting equation (11) into equation (10) gives:

$$\begin{bmatrix} A & B \\ C & D \end{bmatrix} \cdot \begin{bmatrix} v_b \\ v_i \end{bmatrix} = \begin{bmatrix} I_b \\ 0 \end{bmatrix} \quad (12)$$

Expanding equation (12) gives (inter alia):

$Cv_b + Dv_i = 0$, which rearranges to:

$$v_i = -D^{-1} C v_b \quad (13)$$

Inspection of equation (13) shows that all quantities on the right side of the equation are known, or are calculable from known quantities. Specifically, $v_b$ is the vector of measured potential points 104, C is a matrix of values calculable from equation (1A) or equation (1B), and $D^{-1}$ is an inverse matrix, also of values calculable from equations (1A) or (1B). Processor (FIG. 1) is therefore able to evaluate vector $v_i$, i.e., the potentials at the internal vertices of intermediate mesh 122. As described below, the processor uses this evaluation to generate resultant map 50.

Figure 5:
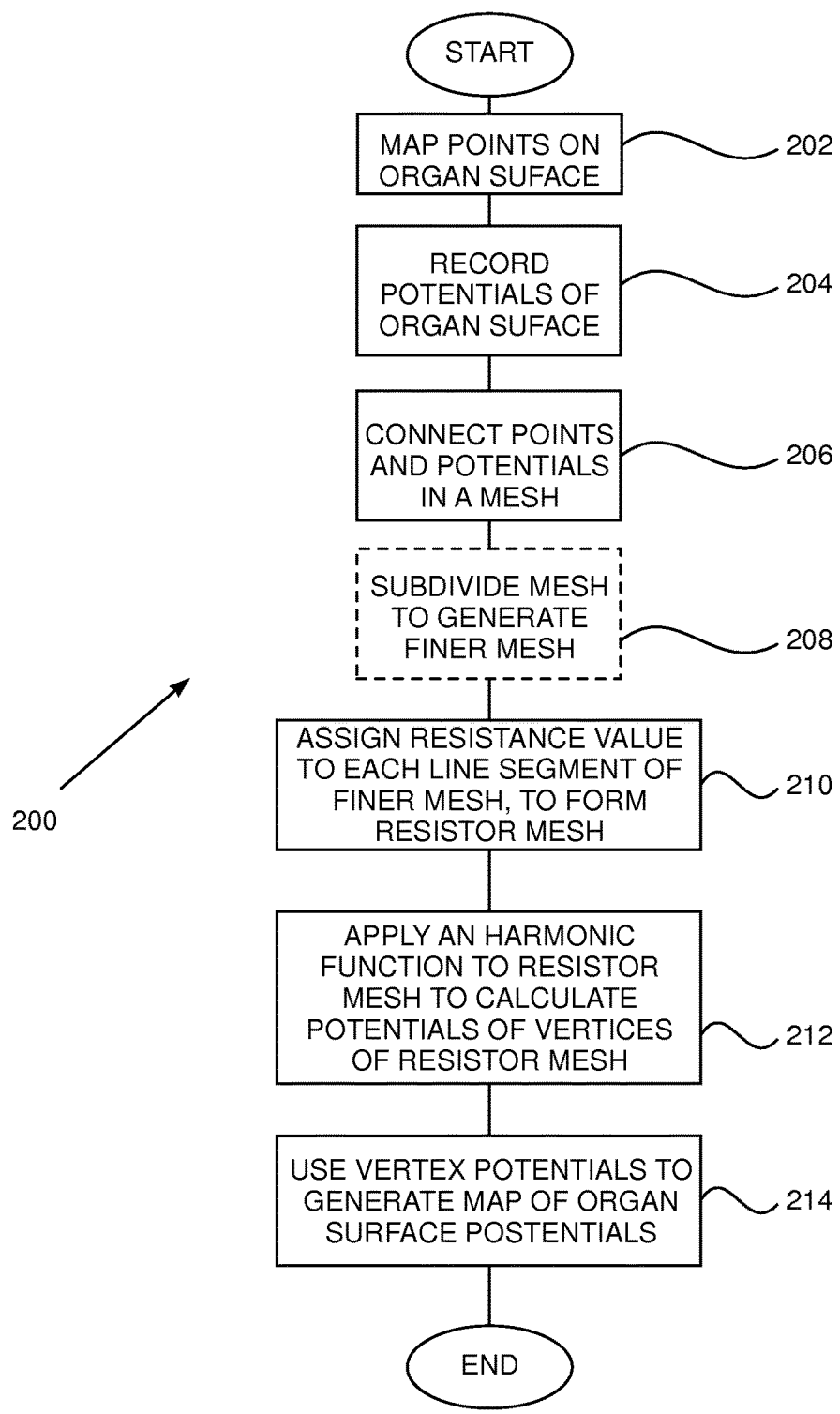
FIG. 5 is a flowchart of steps performed in a procedure for generating an electrophysiological map, according to an embodiment of the present invention.

FIG. 5 is a flowchart 200 of steps performed in a procedure for generating resultant map 50 (FIG. 1), according to an embodiment of the present invention. In an initial mapping step 202, user 28 inserts probe 24 into body organ 34, and uses the distal end of the probe to map, i.e., to generate 3D coordinates, of points on a surface of the organ, as described above with reference to FIG. 1. In step 202 the mapped points correspond to position points 102 referred to above. Processor 40 stores the coordinates of the mapped position points in memory 44.

In a potential measuring step 204, the user uses probe 24 to measure potentials and map the coordinates of points on the surface of organ 34. Step 204 may be performed substantially simultaneously with step 202. Alternatively, the two steps may be performed at different times. The points recorded in step 204 correspond to potential points 104 referred to above. Processor 40 stores the coordinates and measured potentials of the mapped potential points in memory 44.

In a mesh generating step 206, the processor connects the points recorded in steps 202 and 204 as a coarse mesh of line segments. Typically, the mesh is formed as a Delaunay triangulation. A Delaunay triangulation may be generated by starting with an arbitrary triangulation, typically based on constructing Voronoi diagrams from the potential and position points. Within the arbitrary triangulation each pair of triangles sharing a common edge may have the common edge flipped to ensure that the Laplacian or cotangent weight of the edge shared by two triangles is non-negative. Such a method for generating a Delaunay triangulation is well known in the art.

However, there is no necessity that the coarse mesh be in the form of a Delaunay triangulation, so that processor 40 may connect the points using another type of triangulation, or by any convenient method for connecting points, not necessarily using triangulation, known in the art.

In a subdivision step 208, the coarse mesh generated in step 206 is sub-divided into a finer intermediate mesh. Step 208 is optional, as indicated in flowchart 200 by the rectangle for the step being drawn with a dashed perimeter, but for simplicity step 208 is assumed to be implemented in the remaining description of the flowchart. Those having ordinary skill in the art will be able to adapt the description for the case where step 208 is not implemented. The processor may sub-divide the coarse mesh by any convenient method, for example using the method described above with reference to the production of intermediate mesh 122 (FIG. 3). In some embodiments processor 40 may implement the fineness of the subdivision adaptively, according to an amount of time and/or computing resources required for the subdivision and succeeding steps of the procedure.

In a resistor mesh step 210, the processor assumes each line segment of the finer intermediate mesh generated in step 208 is a resistor. The processor calculates a resistance value for each resistor according to equation (1A) or equation (1B), using the length of the corresponding line segment, so that the resistance value assigned to a given line segment is directly proportional to the length of the line segment. The processor connects the resistors according to the connections of the finer intermediate mesh produced in step 208, so that there is a one-to-one correspondence between the vertices and resistors of the resistor mesh and the vertices and line segments of the intermediate mesh.

In a calculation step 212, the processor applies an harmonic function, typically by applying Kirchhoff's current law, to the resistor mesh in order to calculate the potentials at vertices of the resistor mesh corresponding to vertices of the intermediate mesh that are not potential points 104. The application of the law, and the calculation, is according to equation (13).

In a final step 214, the processor uses the vertex potentials calculated in step 212, as well as the measured potentials of potential points 104, to generate resultant map 50 values of the electrophysiological parameters, i.e., $V_{LAT}$s in the example described herein. Typically the map is colored according to the values of $V_{LAT}$. Typically the processor applies interpolation between the potentials in order to generate resultant map 50.

The method outlined herein applies an harmonic function to generate potentials at points on the surface of an organ (exemplified above by the heart) that have not been measured. The inventor believes that because the method uses applicable physical laws, e.g., Kirchhoff's laws, this method generates more accurate values than methods for generating potentials known in the art. In addition, the inventor believes that using the method described herein allows the generation of accurate values of potentials using fewer measured points than those required for methods known in the art.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A method for forming an electropotential map, comprising:
   measuring locations of points on a surface of a body organ;
   measuring electrical potentials of a subset of the points;
   assigning respective resistances to line segments joining the points so as to define a resistor mesh; and
   generating an electropotential map of the surface by applying an harmonic function to the resistor mesh responsive to the measured electrical potentials.

2. The method according to claim 1, wherein the body organ comprises a heart of a human subject.

3. The method according to claim 2, wherein the electropotential map comprises a map of respective potentials associated with local activation times of the heart.

4. The method according to claim 1, wherein measuring the locations comprises inserting a probe into the body organ, and tracking a distal end of the probe in contact with the surface.

5. The method according to claim 4, wherein the distal end comprises tracking coils located therein, and wherein tracking the distal end comprises receiving and analyzing signals from the tracking coils.

6. The method according to claim 4, wherein the distal end comprises an electrode attached thereto, and wherein measuring the electrical potentials comprises measuring the electrical potentials using the electrode.

7. The method according to claim 6, wherein tracking the distal end comprises measuring an impedance between the electrode and electrodes attached to skin of a human subject having the body organ.

8. The method according to claim 1, and comprising forming the line segments as a triangular mesh.

9. The method according to claim 1, wherein the line segments have respective lengths, and wherein assigning the respective resistances comprises assigning the respective resistances to be directly proportional to the respective lengths.

10. The method according to claim 1, wherein applying the harmonic function comprises applying a Kirchhoff's circuit law to the resistor mesh.

11. The method according to claim 10, wherein the Kirchhoff's circuit law comprises Kirchhoff's current law.

12. The method according to claim 10, wherein generating the electropotential map comprises using the Kirchhoff's circuit law to determine electrical potentials of the points on the surface not in the subset.

13. Apparatus for forming an electropotential map, comprising:
   (a) a probe configured to:
      (i) measure locations of points on a surface of a body organ, and
      (ii) measure electrical potentials of a subset of the points; and
   (b) a processor configured to:
      (i) assign respective resistances to line segments joining the points so as to define a resistor mesh,
      (ii) apply a harmonic function to the resistor mesh responsive to the measured electrical potentials; and
      (iii) generate an electropotential map of the surface of the body organ using the resistor mesh and the harmonic function.

14. The apparatus according to claim 13, wherein the body organ comprises a heart of a human subject.

15. The apparatus according to claim 14, wherein the electropotential map comprises a map of respective potentials associated with local activation times of the heart.

16. The apparatus according to claim 13, wherein the processor is configured to track a distal end of the probe inserted into the body organ and in contact with the surface.

17. The apparatus according to claim 16, wherein the distal end comprises tracking coils located therein, and wherein tracking the distal end comprises receiving and analyzing signals from the tracking coils.

18. The apparatus according to claim 16, wherein the distal end comprises an electrode attached thereto, and wherein measuring the electrical potentials comprises measuring the electrical potentials using the electrode.

19. The apparatus according to claim 18, wherein tracking the distal end comprises measuring an impedance between the electrode and electrodes attached to skin of a human subject having the body organ.

20. The apparatus according to claim 13, and comprising forming the line segments as a triangular mesh.

21. The apparatus according to claim 13, wherein the line segments have respective lengths, and wherein assigning the respective resistances comprises assigning the respective resistances to be directly proportional to the respective lengths.

22. The apparatus according to claim 13, wherein applying the harmonic function comprises applying a Kirchhoff's circuit law to the resistor mesh.

23. The apparatus according to claim 22, wherein the Kirchhoff's circuit law comprises Kirchhoff's current law.

24. The apparatus according to claim 22, wherein generating the electropotential map comprises using the Kirchhoff's circuit law to determine electrical potentials of the points on the surface not in the subset.

* * * * *